United States Patent
Dresen et al.

(10) Patent No.: US 10,456,945 B2
(45) Date of Patent: Oct. 29, 2019

(54) TOOL FOR MANUALLY OPERATING OSCILLATING MOTORIZED TOOL ACCESSORY

(71) Applicants: Robert Bosch Tool Corporation, Broadview, IL (US); Robert Bosch GmbH, Stuttgart (DE)

(72) Inventors: Frederik Dresen, Frauenfeld (CH); Creighton Wade Nachtigall, Chicago, IL (US); Christopher A. Nowacki, Long Grove, IL (US); Kenneth C. Osberg, Lake in the Hills, IL (US); Bobby Brent Boyd, Schaumburg, IL (US)

(73) Assignees: Robert Bosch Tool Corporation, Broadview, IL (US); Robert Bosch GmbH, Stuttgart (DE)

( * ) Notice: Subject to any disclaimer, the term of this patent is extended or adjusted under 35 U.S.C. 154(b) by 738 days.

(21) Appl. No.: 14/980,876

(22) Filed: Dec. 28, 2015

(65) Prior Publication Data

US 2016/0184984 A1 Jun. 30, 2016

Related U.S. Application Data

(60) Provisional application No. 62/097,398, filed on Dec. 29, 2014.

(51) Int. Cl.
*B27B 19/00* (2006.01)
*B24B 23/04* (2006.01)
(Continued)

(52) U.S. Cl.
CPC .......... *B27B 19/006* (2013.01); *A61B 17/142* (2016.11); *B23D 51/10* (2013.01); *B24B 23/04* (2013.01); *B25F 3/00* (2013.01); *B26B 5/00* (2013.01); *A61B 17/144* (2016.11); *B23D 61/006* (2013.01); *B26B 7/00* (2013.01); *B27F 5/00* (2013.01); *Y10T 279/17769* (2015.01); *Y10T 279/3406* (2015.01)

(58) Field of Classification Search
CPC ... B23B 31/008; B23B 31/107; B23B 49/003; B26B 5/00; B26B 7/00; B25F 3/00; B25F 5/00; B23D 51/08; B23D 51/10; B23D 61/006; A61B 17/14; A61B 17/142; A61B 17/144; Y10T 279/17769; Y10T 279/3406
USPC ..... 173/29, 170, 217, 49, 90; 30/164.9, 169, 30/171, 272.1, 277.4, 351, 339; 279/143; 606/171, 176, 178, 79; 15/236.01; 451/359, 509
See application file for complete search history.

(56) References Cited

U.S. PATENT DOCUMENTS 1,964,947 A * 7/1934 Hentschel .............. B27G 17/04
30/171
2,257,314 A * 9/1941 Shinn, Jr. ................ A47L 13/08
15/236.01

(Continued)

*Primary Examiner* — Scott A Smith
(74) *Attorney, Agent, or Firm* — Maginot Moore & Beck LLP

(57) ABSTRACT

A tool system for use with an accessory tool including a mounting end, comprises an oscillating power tool and a handheld tool assembly. The oscillating power tool includes a first tool holder configured to connect to the mounting end of the accessory tool. The handheld tool assembly includes a second tool holder configured to connect to the mounting end of the accessory tool.

11 Claims, 14 Drawing Sheets

(51) Int. Cl.
  *B26B 5/00* (2006.01)
  *A61B 17/14* (2006.01)
  *B23D 51/10* (2006.01)
  *B25F 3/00* (2006.01)
  *B23D 61/00* (2006.01)
  *B27F 5/00* (2006.01)
  *B26B 7/00* (2006.01)

(56) References Cited

U.S. PATENT DOCUMENTS

| | | | |
|---|---|---|---|
| 4,106,181 A | 8/1978 | Mattchen | |
| 4,199,852 A * | 4/1980 | Ayers | B25B 27/0035 29/239 |
| 4,381,604 A * | 5/1983 | Horst | B44D 3/164 15/236.01 |
| 4,395,825 A * | 8/1983 | Lock | B25D 17/02 29/275 |
| 4,481,689 A * | 11/1984 | Westmoreland | B44D 3/164 15/236.01 |
| 4,727,941 A * | 3/1988 | Fulton | B23D 57/0076 173/114 |
| 4,989,320 A * | 2/1991 | Borkott | B23D 35/008 30/162 |
| 5,058,273 A * | 10/1991 | Streger | B23D 51/10 30/164.9 |
| 5,122,142 A * | 6/1992 | Pascaloff | A61B 17/144 606/171 |
| 5,440,811 A * | 8/1995 | Challis | B25G 3/26 30/169 |
| 6,112,420 A | 9/2000 | Schickerling | |
| 6,651,346 B1 | 11/2003 | Sturgis et al. | |
| 6,715,210 B2 | 4/2004 | Chao | |
| 6,802,127 B2 * | 10/2004 | Thomaschewski | B26B 7/00 30/272.1 |
| 6,945,862 B2 * | 9/2005 | Jasch | B23B 31/008 451/342 |
| 7,189,239 B2 * | 3/2007 | Fisher | B23D 51/10 606/176 |
| 7,607,706 B2 | 10/2009 | Cunningham et al. | |
| 7,726,664 B2 | 6/2010 | Peters | |
| 7,789,885 B2 * | 9/2010 | Metzger | A61B 17/155 606/88 |
| 7,814,608 B1 | 10/2010 | Catello | |
| 8,356,415 B2 | 1/2013 | Lin | |
| 8,365,419 B2 | 2/2013 | Bernardi et al. | |
| 8,387,717 B2 * | 3/2013 | Kildevaeld | B23D 51/10 173/1 |
| 8,616,562 B2 * | 12/2013 | Maras | B25F 3/00 279/143 |
| 2009/0188066 A1 * | 7/2009 | Van Deursen | A47L 13/022 15/236.01 |
| 2011/0067894 A1 * | 3/2011 | Bernardi | B25B 28/00 173/1 |
| 2011/0072946 A1 * | 3/2011 | Bernardi | B25F 5/00 83/522.11 |

\* cited by examiner

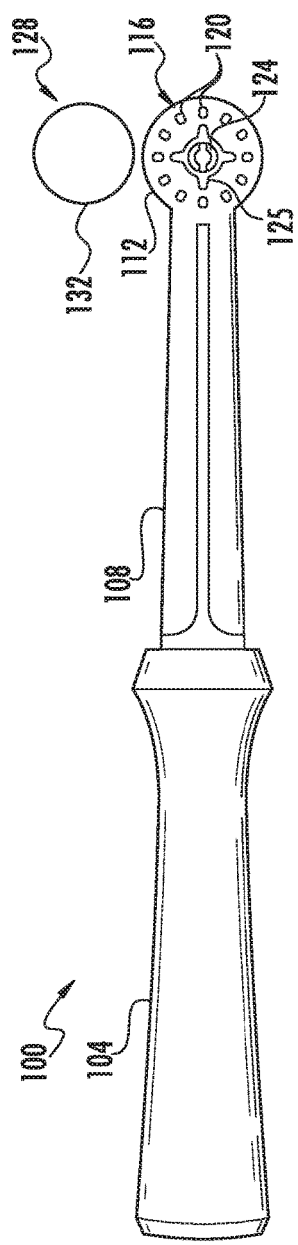
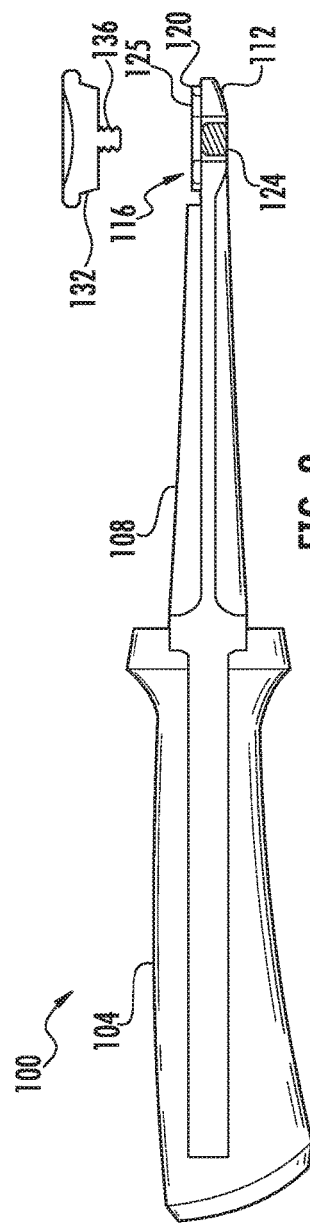
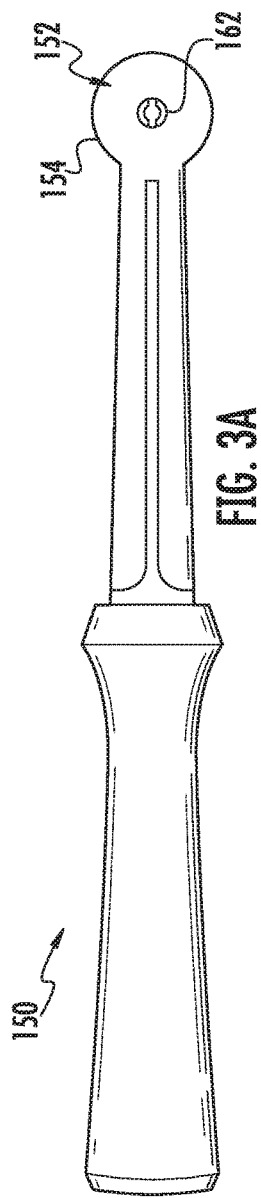

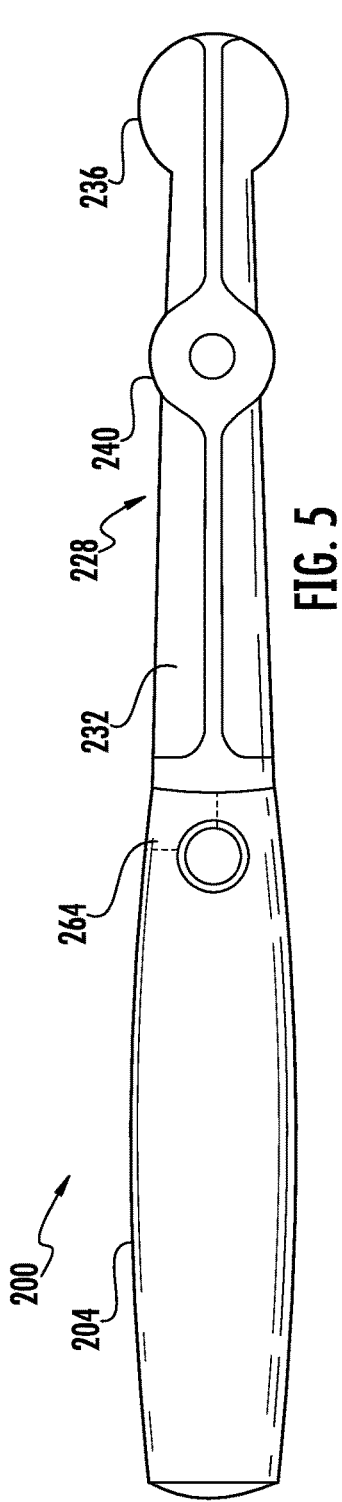
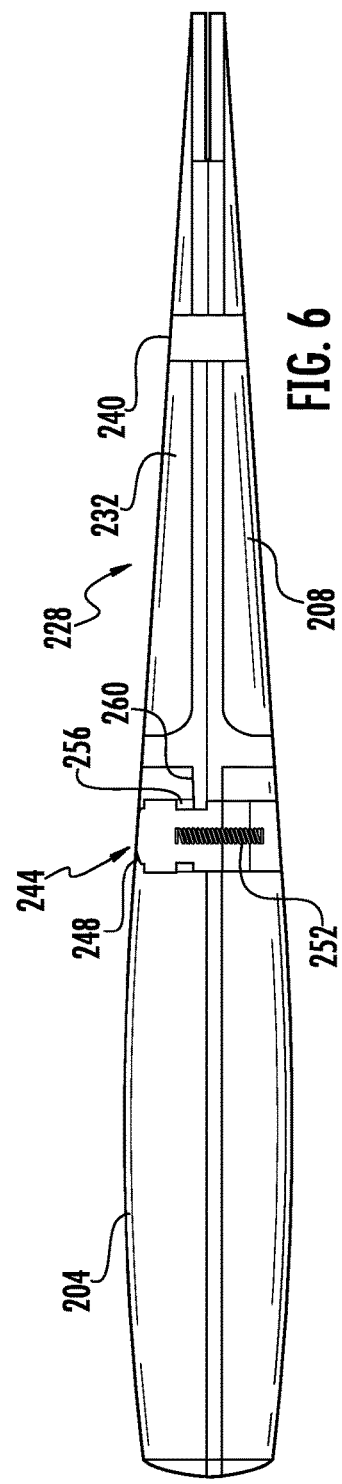
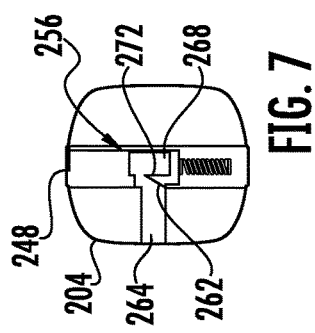

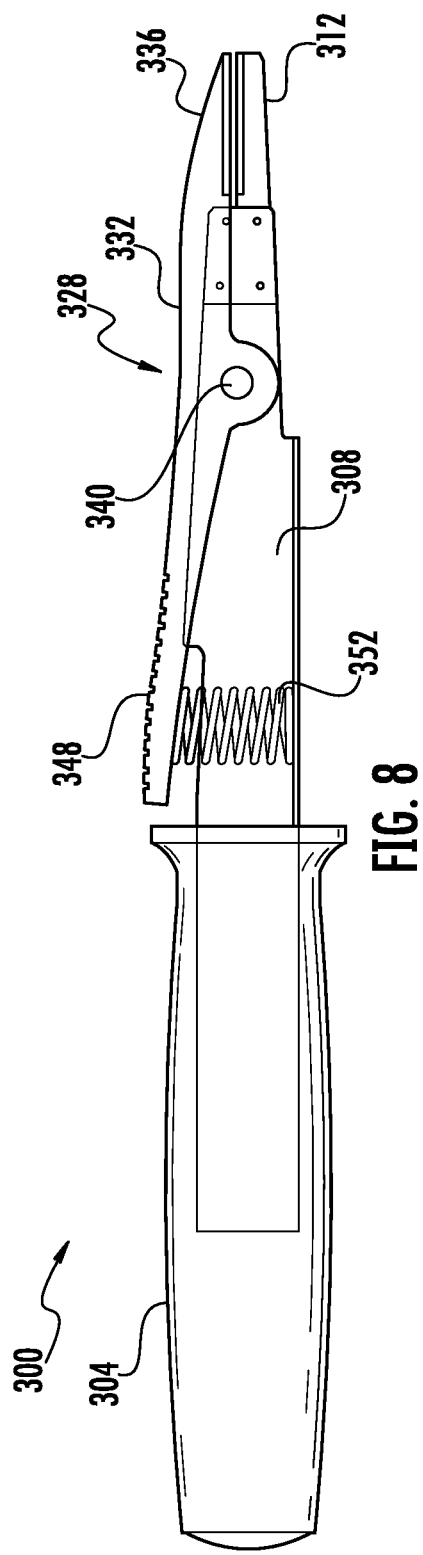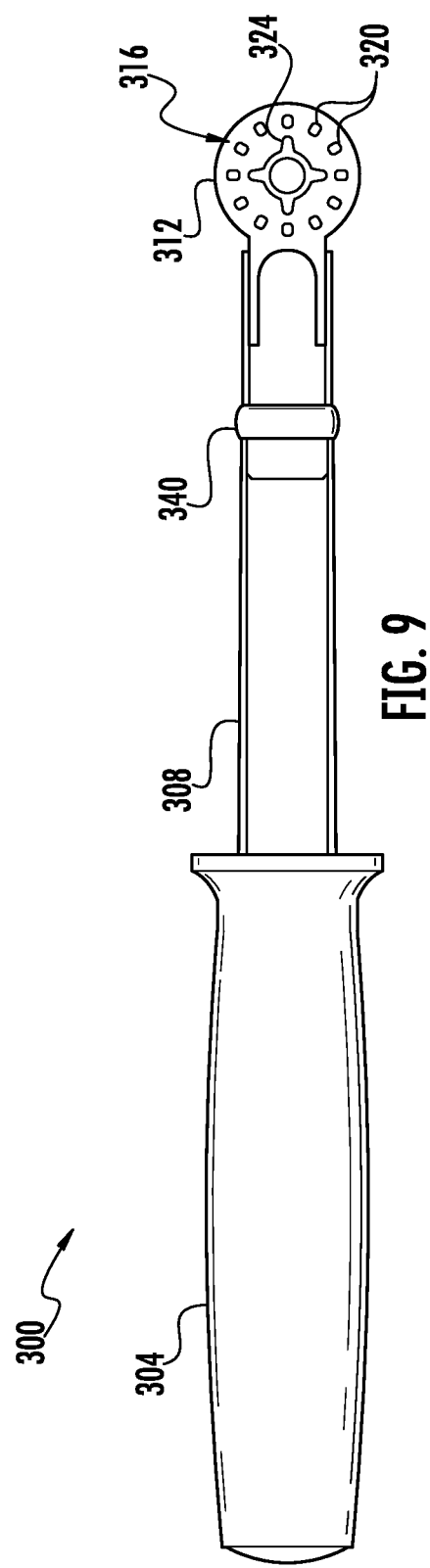

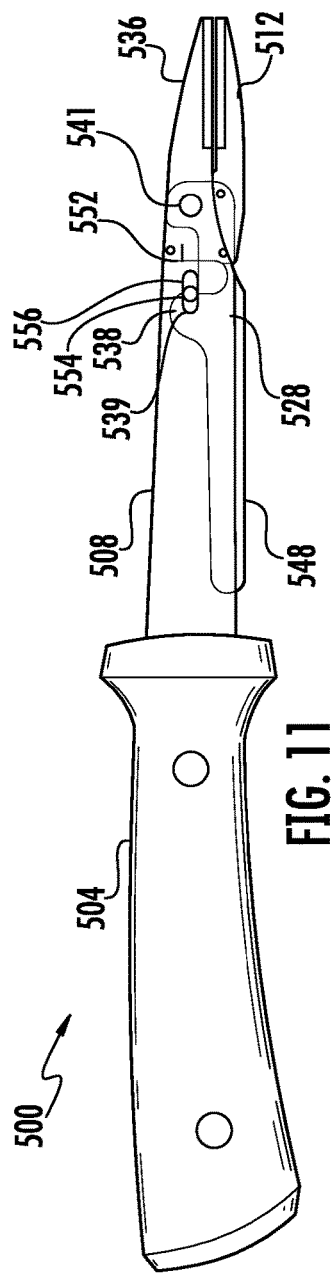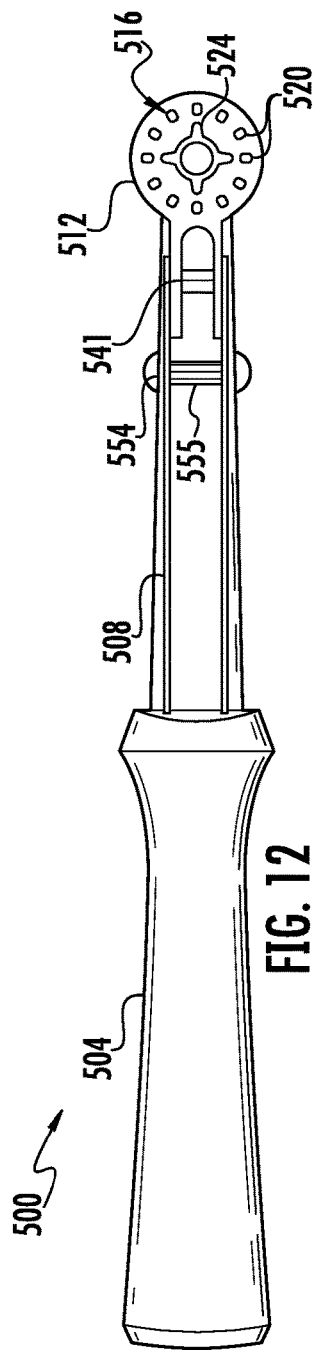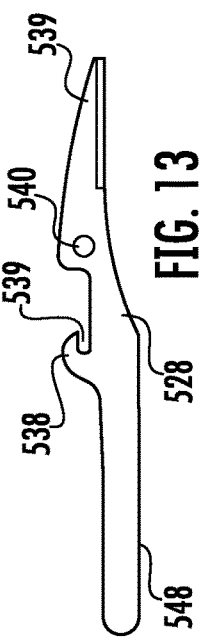

TOOL FOR MANUALLY OPERATING OSCILLATING MOTORIZED TOOL ACCESSORY

This application claims the benefit of priority of U.S. provisional application Ser. No. 62/097,398, filed on Dec. 29, 2014 the disclosure of which is herein incorporated by reference in its entirety.

The disclosure relates to the field of handheld tools, and more particularly manually operated handheld tools for use with tool accessories.

BACKGROUND

Oscillating power tools, such as oscillating motorized tools, are lightweight, motorized handheld tools configured to oscillate various accessory tools, attachments, and bits, such as cutting blades, sanding discs, grinding tools, and many others. The accessory tools enable an oscillating power tool to be used to shape and contour workpieces of various materials in a wide variety of ways. Accessory tools mount to an oscillating power tool using a machine screw or a quick-change mechanism.

Oscillating power tool end users often encounter scenarios in which manual operation of the accessory tool without oscillatory movement can be useful. For example, a user may find manual operation of the accessory tool without the oscillatory movement sufficient, easier, or even more effective than utilizing the oscillatory movement in order shape or contour a workpiece in various situations. In one particular example, when using a cutting blade accessory tool, delicate or finishing work could demand only slight movement of the cutting blade whereby full oscillation of the cutting blade by the oscillating power tool would be excessive, or could cause unintended damage the workpiece. In another particular example, a user may wish to utilize the sharp end of a cutting blade accessory tool to scrape or cut a portion of a workpiece with precision or by applying a specific amount of force or torque against the workpiece with the accessory tool, which could not otherwise be achieved while operating the oscillating power tool to oscillate the accessory tool.

However, due to the configuration of previously known oscillating tools, manual operation of the oscillating tools has drawbacks. For example, the handle area of an oscillating power tool is often a part of the housing that contains the motor, which can be cumbersome and uncomfortable to hold. The size of the housing may also prevent the accessory tool from entering a tight workspace that the user wishes to work with the accessory tool, such as at an inside corner of a workpiece. The accessory tool additionally can inconveniently pivot about the end of the oscillating power tool upon which the accessory tool is mounted when the user presses the accessory tool into contact with a workpiece. The pivoting motion can make the position of the accessory tool difficult to control and maneuver. When the pivoting occurs, the torque applied by the user's hand to the housing may not be fully transmitted to the workpiece, or transmitted in a varying manner, unpredictable manner. The end of some oscillating power tools where an accessory tool is mounted is radially offset from the handle portion, which can also make accurate operation of the accessory tool difficult.

Therefore, there is a need for effectively manually operating an accessory tool of an oscillating power tool.

SUMMARY

According to an exemplary embodiment of the disclosure, a tool system for use with an accessory tool including a mounting end, comprises an oscillating power tool and a handheld tool assembly. The oscillating power tool includes a first tool holder configured to connect to the mounting end of the accessory tool. The handheld tool assembly includes a second tool holder configured to connect to the mounting end of the accessory tool.

According to another exemplary embodiment of the disclosure, a method of operating a tool system including an oscillating power tool, a handheld tool assembly, and an accessory tool for shaping a workpiece, comprises connecting the accessory tool to a first tool holder of one of the oscillating power tool and the handheld tool assembly, using the accessory tool connected to the first tool holder to shape a workpiece, disconnecting the accessory tool from the first tool holder, connecting the accessory tool to a second tool holder of the other of the oscillating power tool and the handheld tool assembly, and using the accessory tool connected to the second tool holder to continue shaping the workpiece.

BRIEF DESCRIPTION OF THE DRAWINGS

The above-described features and advantages, as well as others, should become more readily apparent to those of ordinary skill in the art by reference to the following detailed description and the accompanying figures in which:

FIG. 1B depicts a top perspective view of the handheld tool assembly of FIG. 1A that is configured to enable manual operation of the accessory tool, the handheld tool assembly comprising a handle, a tool shaft, a tool holder having a mounting structure with protrusions and a tab, and a clamping mechanism having a threaded pin that may be tightened to a tool holder to secure the accessory tool to the tool holder.

FIG. 2 depicts a side, cross-sectional view of the handheld tool assembly of FIG. 1B.

FIG. 3A depicts a top perspective view of another embodiment of the handheld tool assembly that utilizes the clamping mechanism of the embodiment of FIG. 1B and has a tool holder with a mounting structure that lacks protrusions and a tab.

FIG. 5 depicts a top perspective view of the handheld tool assembly of FIG. 4 with the clamping mechanism in the locked position.

FIG. 6 depicts a side, cross-sectional view of the handheld tool assembly of FIG. 4 in the locked position.

FIG. 7 depicts a rear, partial cross-sectional view of the handle of the handheld tool assembly of FIG. 4 showing the slot of the handle and opening in the actuator button.

FIG. 8 depicts a side, cross sectional view of another embodiment of a handheld tool assembly having a clamping mechanism shown in a locked position that is pivotable about a horizontal axis in order to selectively mount an accessory tool.

FIG. 9 depicts a cutaway top view of the handheld tool assembly of FIG. 8 with the clamping mechanism removed to show the tool holder.

FIG. 11 depicts a side perspective view of another embodiment of a handheld tool assembly with a clamping mechanism shown in a locked position that is selectively locked by actuating a pin within a slot.

FIG. 12 depicts a cutaway top view of the handheld tool assembly of FIG. 11 with the clamping mechanism removed to show the tool holder.

FIG. 13 depicts a side perspective view of the clamping mechanism of the handheld tool assembly of FIG. 11 removed from the handle and tool shaft.

DETAILED DESCRIPTION

Figure 1A:
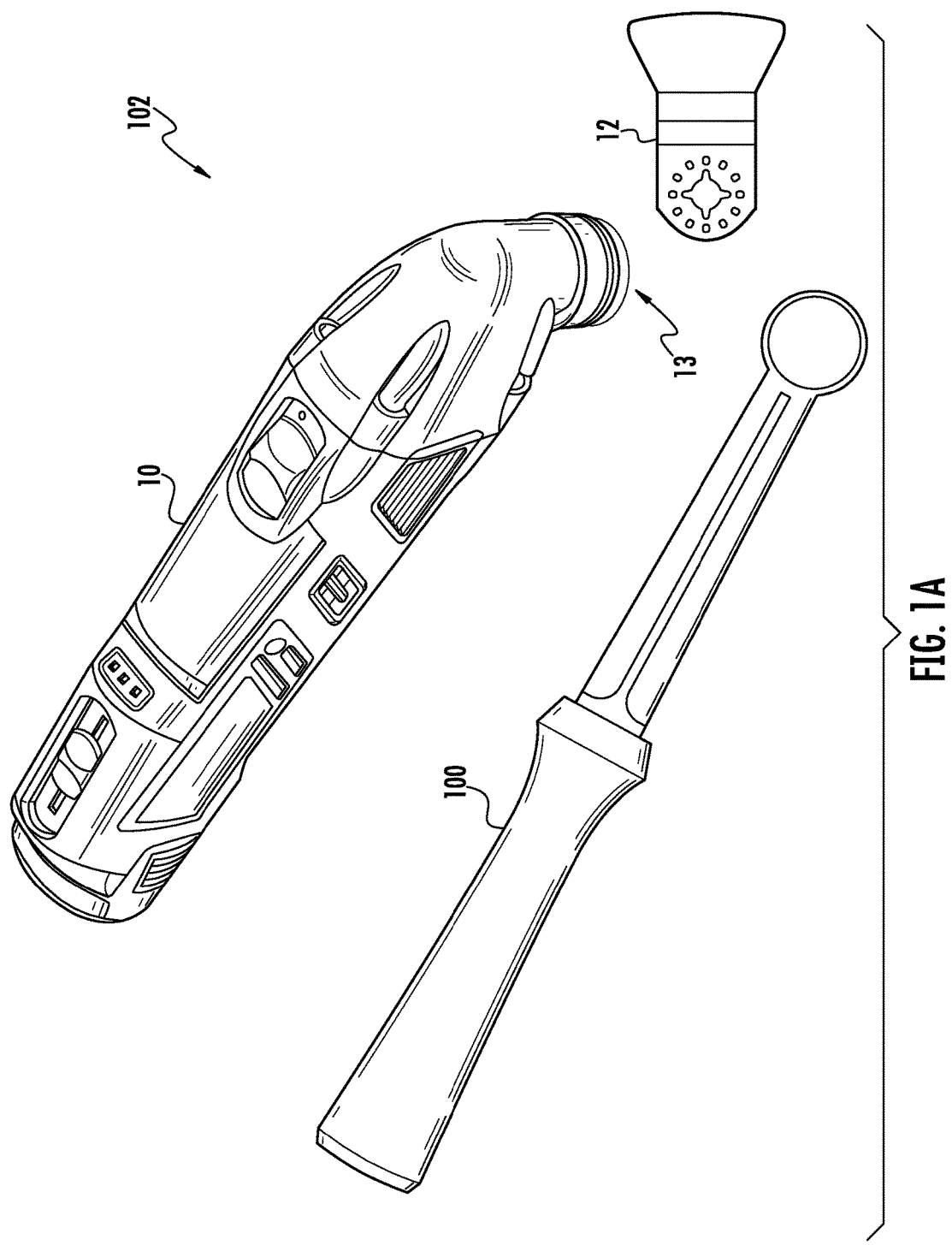
FIG. 1A depicts a tool system including an oscillating motorized tool and a handheld tool assembly for use with an accessory tool.

For the purposes of promoting an understanding of the principles of the disclosure, reference will now be made to the embodiments illustrated in the drawings and described in the following written specification. It is understood that no limitation to the scope of the disclosure is thereby intended. It is further understood that the disclosure includes any alterations and modifications to the illustrated embodiments and includes further applications of the principles of the disclosure as would normally occur to one of ordinary skill in the art to which this disclosure pertains.

Figure 24:
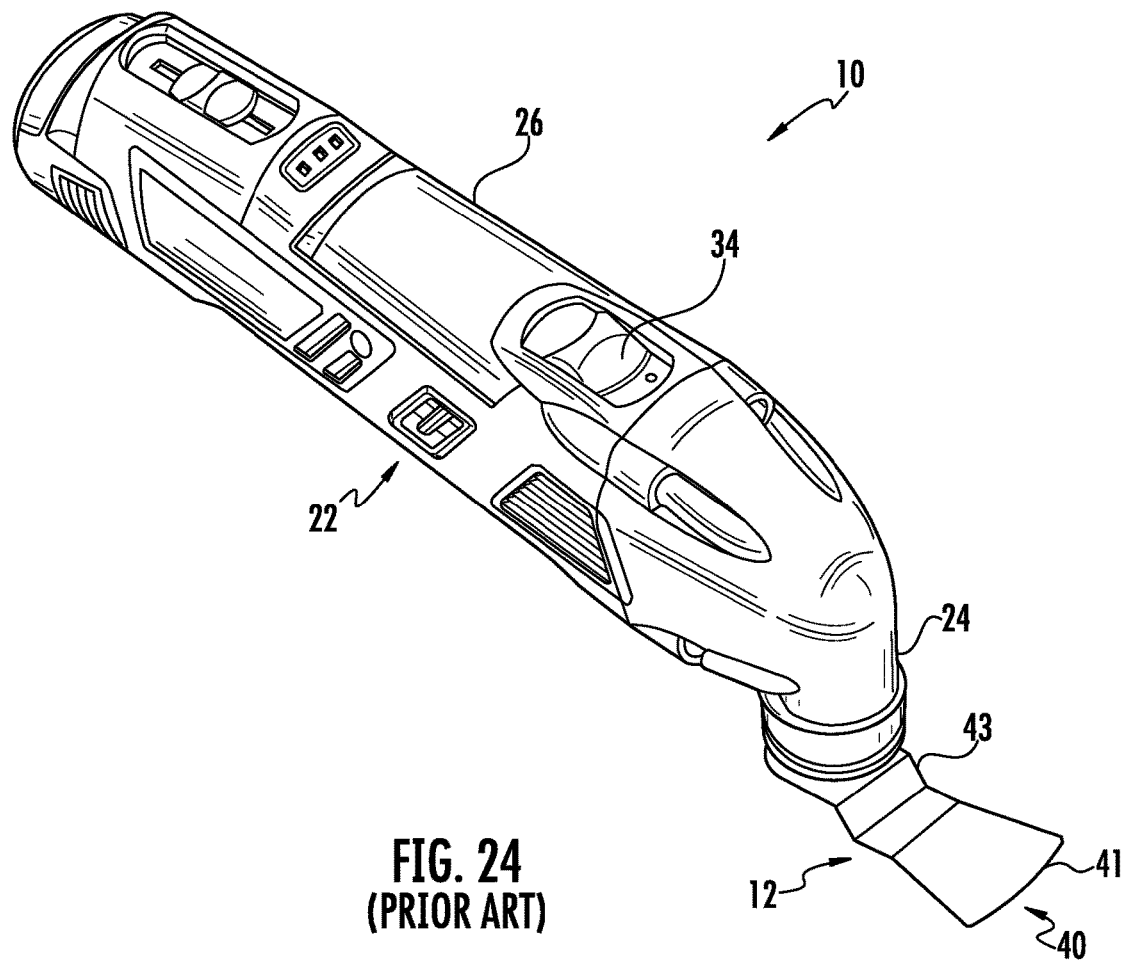
FIG. 24 depicts a perspective view of a previous oscillating motorized tool with an accessory tool.

FIG. 24 depicts a previous oscillating tool 10 for driving an accessory tool, such as the accessory tool 12 shown, including a generally cylindrically-shaped housing 22 having a handle portion 26 and a nose portion 24. The handle portion 26 encloses a motor (not shown), such as an electric motor, which is configured to receive power from a rechargeable battery (not shown) or from an AC outlet via a power cord (not shown). Power to the motor is controlled by a power switch 34 provided on the handle portion 26 of the housing 22. The motor is configured to oscillate a drive member (not shown) and a tool holder 13 to which the accessory tool 12 is operably connected, thereby oscillating the accessory tool 12. The tool holder 13 is adjacent to the nose portion 24.

Figure 25:
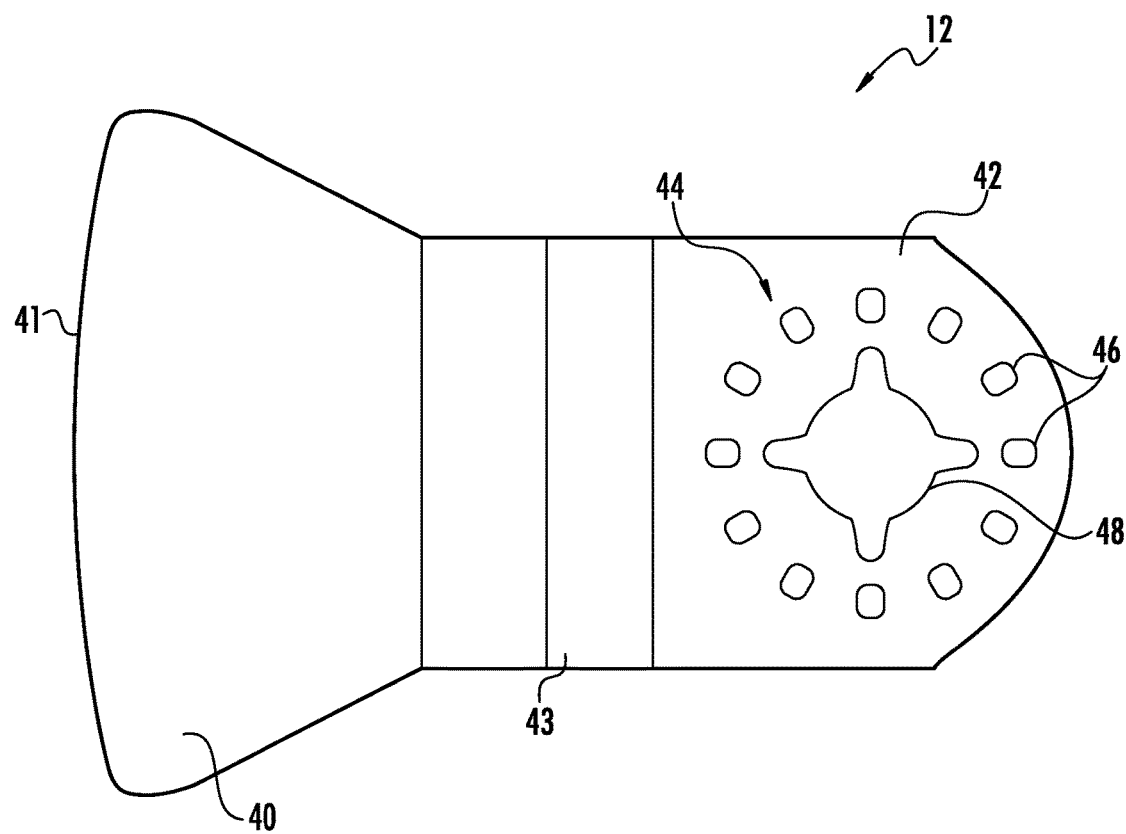
FIG. 25 depicts a top perspective view of the accessory tool of FIG. 24.

Turning to FIG. 25, the accessory tool 12 includes a working end 40 configured to engage a workpiece, a mounting end 42 configured to be secured to an oscillating tool, and a transition region 43 (best shown in FIG. 24) that offsets the working end 40 from the mounting end 42. In the embodiment shown, the working end 40 is embodied as a blade 41 configured to cut, or scrape a workpiece. The mounting end 42 includes a mounting structure 44 having a plurality of openings or recesses 46 and a central opening 48 that are sized, shaped, and positioned complementary to protrusions and a central bore, respectively, of a mounting structure of an oscillating tool (not shown in FIG. 24). The protrusions are arranged in a desired configuration.

As mentioned, oscillating power tool end users often encounter scenarios in which manual operation of the accessory tool without the oscillatory movement can be useful, and operating an accessory tool that is mounted to an oscillating power tool manually with the motor switched off has drawbacks.

FIG. 1A depicts a tool system 102 including the oscillating tool 10 and a handheld tool assembly 100 both of which are configured for use with the accessory tool 12. FIGS. 1B and 2 depict the handheld tool assembly 100, which is configured to enable manual operation of the accessory tool 12. The handheld tool assembly 100 includes a handle 104 fixedly secured to a tool shaft 108. The opposite end of the tool shaft 108 includes a tool holder 112 having a mounting structure 116 extending from the tool shaft 108. The mounting structure 116 fixedly extends from the tool shaft 108 and includes a plurality of protrusions 120 arranged in the same configuration as the protrusions of the oscillating tool 10. For example, in one embodiment, the protrusions 120 are arranged in a circular pattern about a central threaded bore 124 and tab 125 that are sized, shaped, and positioned complementary to the openings or recesses 46 and the central opening 48 of the accessory mounting structure 44 of the accessory tool 12 of FIG. 25. The handheld tool assembly 100 further includes a clamping member 128 configured to secure an accessory tool, such as the accessory tool 12 of FIG. 25, having a knob 132 and a threaded pin 136 (shown in FIG. 2) that is configured to cooperate with threads of the threaded bore 124.

In order to mount the accessory tool 12 of FIG. 25 to the handheld tool assembly 100, the mounting end 42 of the accessory tool 12 is placed on the tool holder 112 (FIG. 1B) such that the protrusions 120 and the tab 125 of the mounting structure 116 (FIG. 1B) are received in the corresponding openings and/or recesses 46 and opening 48, respectively, of the accessory tool 12 (FIG. 25), with the opening 48 of the accessory tool 12 (FIG. 25) aligned with the central bore 124 of the mounting structure 116 (FIG. 1B). The threaded pin 136 (FIG. 2) of the clamping member 128 is then aligned with the opening 48 (FIG. 25) of the accessory tool 12 and the central bore 124 (FIG. 1B) of the mounting structure 116 and the knob 132 is rotated until the clamping member 128 is fully tightened against the accessory tool 12 to secure the accessory tool in place against the tool holder 112. When the accessory tool 12 is connected to the tool holder 112, the accessory tool 12 is prevented from moving relative to the handle 104.

It is noted that while the mounting structure 116 has been described as having a plurality of protrusions 120 as shown in FIG. 1B that mate with corresponding openings or recesses of the accessory tool 12 shown in FIG. 12, in other embodiments, the mounting structure only includes a single protrusion, two protrusions, or any desired number of protrusions to cooperate with any of the corresponding openings and/or recesses of the accessory tool 12. In some embodiments, the mounting structure includes one or more tabs shaped to cooperate with the opening 48 of the accessory tool 12 (FIG. 25). In one particular embodiment shown in FIG. 3A, a handheld tool assembly 150 is substantially similar to the handheld tool assembly 100 of FIGS. 1B and 2, except a tool holder 154 has a mounting structure 152 that lacks any protrusions or a tab. The tool holder instead only has a threaded opening 162, similar to the opening 124 of the handheld tool assembly 100 of FIGS. 1B and 2, configured to receive the threaded pin 136 of the clamping member 128 (FIG. 1B). The accessory tool is placed on a tool holder 154, and a holding force applied to the accessory tool by tightening the clamping member 128 (FIG. 1B) is sufficient to secure the accessory tool even without protrusions or a tab that mate with the recesses or opening of the accessory tool, such as the accessory tool 12 of FIG. 25. Any of the embodiments of a handheld tool assembly of the disclosure similarly can have any desired number of protrusions, tabs, or no protrusions or tabs at all to secure the accessory tool 12.

Additionally, it should be understood that while reference is made to the accessory tool 12 of FIG. 25 having the specific working end and mounting structure shown and described, any accessory tool for an oscillating power tool having any desired type of working end and mounting structure may be secured to a handheld tool assembly. The mounting structure of the handheld tool assembly can be designed to correspond and mate with any working end and mounting structure of a desired accessory tool. Therefore, embodiments of the handheld tool assembly depicted in FIGS. 1B and 2, as well as any of the other embodiments shown in the Figures and described in the disclosure, are not restricted to securing the specific accessory tool 12 shown in FIG. 25 with the specific mounting structure depicted. Each of the embodiments of the handheld tool assembly of the disclosure can be configured to secure oscillating tool accessory tools having any desired type of working end, and any desired type of mounting structure.

In some embodiments, the tool system 102 includes the accessory tool 12, the oscillating tool 10, and the handheld tool assembly 100.

Figure 3B:
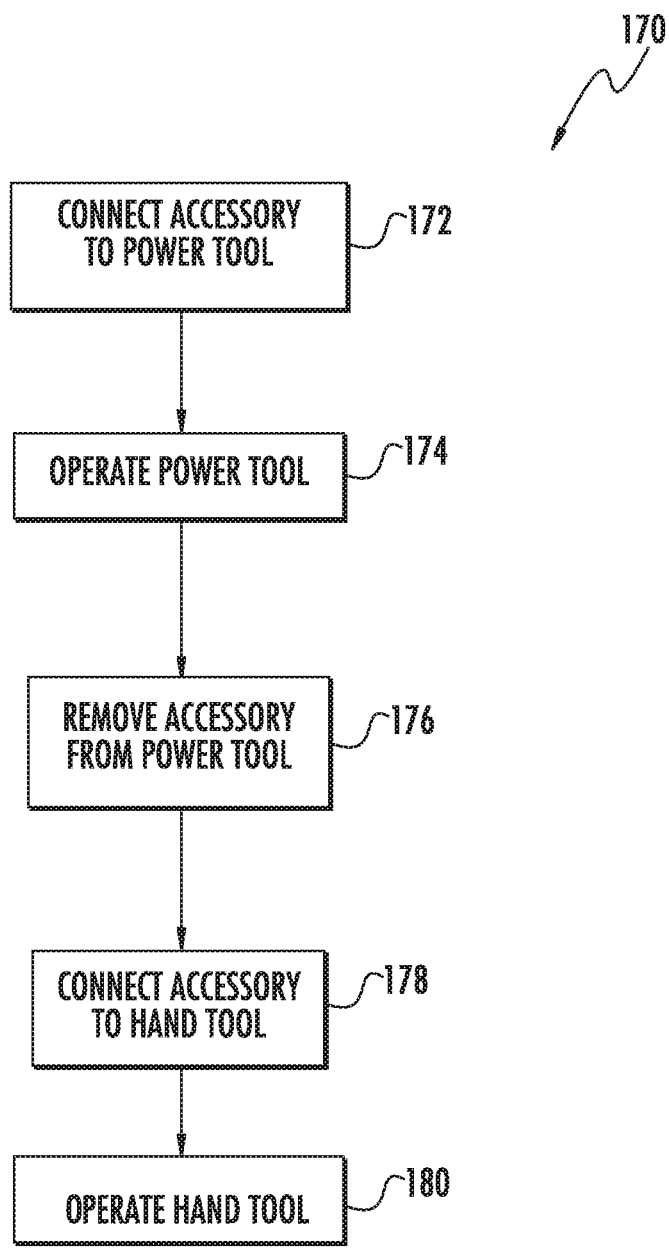
FIG. 3B depicts a flowchart showing an exemplary method of operating the tool system of FIG. 1A.

In operation, the tool system 102 of FIG. 1A is operated, in one embodiment, according to the method 170 shown in the flowchart of FIG. 3B. In block 172, the accessory tool 12 is connected to the tool holder 13 of the oscillating tool 10. Next, in block 174 the oscillating tool 10 is operated by supplying electrical power to the tool 10 and making at least a portion of a cut (for example) in a workpiece or partially shaping the workpiece (for example) with the oscillating accessory tool 12. The oscillating tool 10 may also be used in any other way to shape the workpiece, such as by grinding, sanding, polishing, and the like. Accordingly, as used herein the term "shaping" a workpiece includes cutting, grinding, sanding, polishing, and the like.

In block 176, the accessory tool 12 is removed from the tool holder 13 of the oscillating tool 10. The accessory tool 12 is removed from the oscillating tool 10, because, for example, a portion of the cut in the workpiece is difficult or inconvenient to complete using the accessory tool 12 when the accessory tool 12 is connected to the oscillating tool 10. Accordingly, in block 178, in order to more conveniently finish the cut in the workpiece the accessory tool 12 is connected to the tool holder 112 of the handheld tool assembly 100. Then, in block 180, the handheld tool assembly 100 is manipulated or operated to complete the portion of the cut in the workpiece (for example) or to finish shaping the workpiece (for example) using the accessory tool 12 connected to the handheld tool assembly 100. Accordingly, the workpiece is cut using the accessory tool 12 connected to the oscillating tool 10, then the accessory tool 12 is switched to the handheld tool assembly 100 and the cut is completed using the accessory tool 12 connected to the handheld tool assembly 100. The method 170 may also be performed by starting a cut in a workpiece using the accessory tool 12 connected to the handheld tool assembly 100 and then finishing the cut with the accessory tool 12 connected to the oscillating tool 10.

Figure 4:
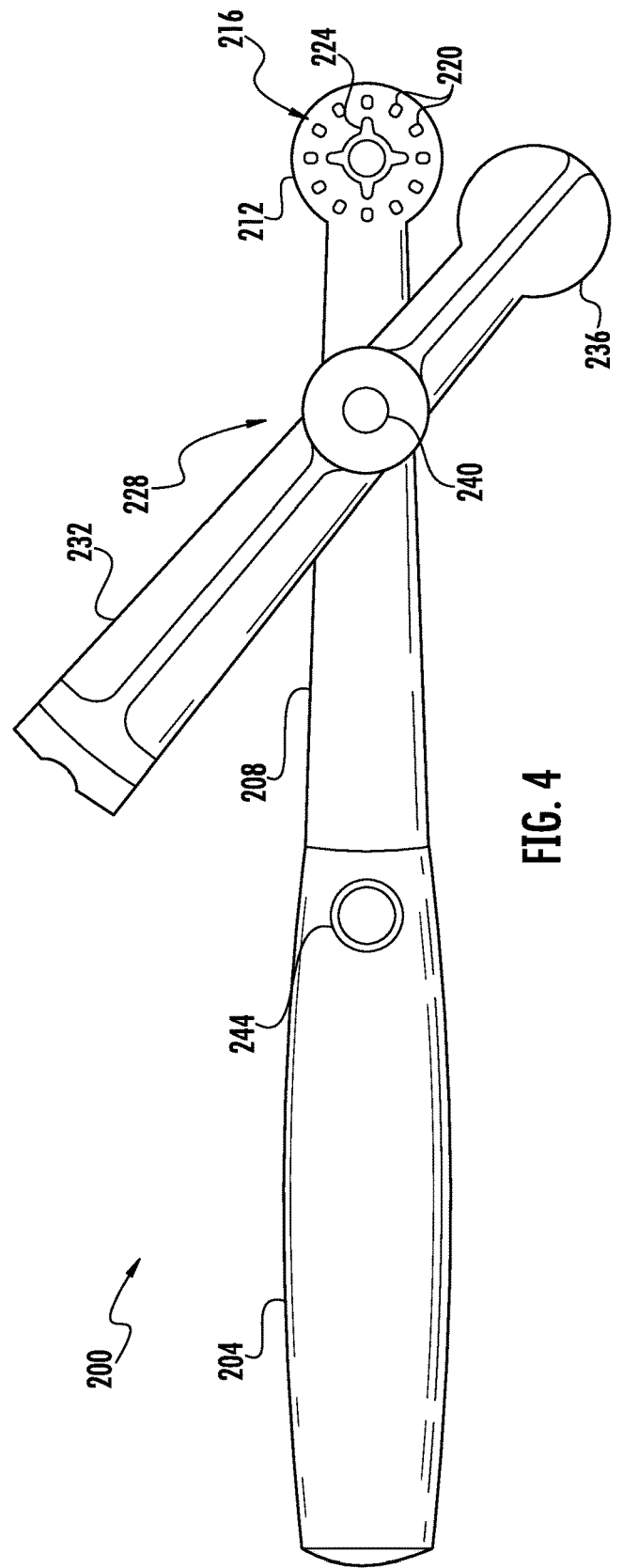
FIG. 4 depicts a top perspective view of another embodiment of a handheld tool assembly having a clamping mechanism shown in an unlocked position that is pivotable about a vertical axis in order to selectively secure an accessory tool.

FIGS. 4-6 depict another embodiment of a handheld tool assembly configured to enable manual operation of an accessory tool. Referring to FIG. 4, a handheld tool assembly 200 includes a handle 204 fixedly secured to a tool shaft 208. The end of the tool shaft 208 includes a tool holder 212 having a mounting structure 216. The mounting structure 216 includes a plurality of protrusions 220 arranged in a circular pattern about a tab 224 that are sized, shaped, and positioned complementary to the openings or recesses 46 and the central opening 48 of the accessory mounting structure 44 of the accessory tool 12 (FIG. 25).

The handheld tool assembly 200 further includes a clamping member 228 configured to secure an accessory tool to the tool holder 212. The clamping member 228 includes a shaft section 232 pivotably mounted to the tool shaft 208 with a pin 240, and a clamping head element 236 configured to retain an accessory tool on the tool holder 212. The shaft 232 is configured to pivot between an unlocked or unclamped position as shown in FIG. 4 in which an accessory tool may be placed on or removed from the mounting structure 216 of the tool holder 212, and a locked or clamped position as shown in FIGS. 5-6 in which the clamping head element 236 aligns with the tool holder 212 to retain an accessory tool.

With reference to FIG. 6, the clamping member 228 further includes a locking projection 260, and the handle 204 includes an actuation mechanism 244 which are together configured to selectably secure the clamping member 228 in the locked position. The actuation mechanism 244 includes a depressible button 248 movable to a locked position and an unlocked position and biased toward the locked position, shown in FIG. 6, by a biasing element 252, shown as a coil spring. An opening 256 is configured to receive the locking projection 260 of the clamping member 228. As shown in FIG. 5, the handle 204 also includes a slot 264 which is aligned with the opening 256 (best shown in FIG. 7) of the actuation mechanism 244. When the handle 204 is pivoted from the unlocked position (FIG. 4) to the locked position (FIGS. 5-6), the projection 260 passes through the slot 264 of the handle 204 (FIGS. 5 and 7), and into the opening 256 of the actuation mechanism 244.

Referring to FIG. 7, when the locking projection 260 (FIG. 6) enters the opening 256 of the actuation mechanism 244, the locking projection 260 engages a ramped surface 262, which forces the button 248 downwards against the biasing force applied by the biasing element 252 until the locking projection 260 aligns with a deeper locking opening 268. The biasing element 252 then forces the button 248 upwards, and a locking surface 272 adjacent the ramped surface 262 prevents the shaft section 232 from being pivoted back to the unlocked position.

In order to move the clamping member 228 back to the unlocked position, the button 248 is depressed until the locking surface 272 no longer blocks the projection 260 (FIG. 6) from entering the slot 264 of the handle 204. The clamping member 228 may then be pivoted back to the unlocked position of FIG. 4. Thus, the actuation mechanism 244 enables movement of the clamping member 228 from the clamped position to the unclamped position when the button 248 is in the unlocked position, and the actuation mechanism 244 prevents movement of the clamping member 228 from the clamped position to the unclamped position when the actuation mechanism 244 is in the locked position.

Although one particular embodiment of the locking and actuation mechanism has been described, it should be understood than any desired locking and actuation mechanism may be utilized in order to secure the clamping head element 236 over the mounting structure of the accessory tool.

FIGS. 8-9 depict another embodiment of a handheld tool assembly configured to enable manual operation of an accessory tool. Referring to FIG. 8, the handheld tool assembly 300 includes a handle 304 fixedly secured to a tool shaft 308. The end of the tool shaft 308 includes a tool holder 312 having a mounting structure 316 (shown in FIG. 9). The mounting structure 316 includes a plurality of protrusions 320 arranged in a circular pattern about a tab 324 that are sized, shaped, and positioned complementary to the openings or recesses 46 and the central opening 48 of the accessory mounting structure 44 of the accessory tool 12 (FIG. 25).

The handheld tool assembly 300 further includes a clamping member 328 configured to secure an accessory tool to the tool holder 312. The clamping member 328 includes a shaft section 332 pivotably mounted to the tool shaft 308 with a pin 340 that extends through openings in both the shaft section 332 of the clamping member 328, and the tool shaft 308 (shown in FIG. 9). The clamping member 328 further includes a clamping head element 336 configured to retain an accessory tool 12 within the mounting structure 316. The shaft 332 is pivotably biased to a locked position (also referred to herein as the clamped position), as shown in FIG. 7, by a biasing element 352 in which the clamping head element 336 is pressed tightly towards the tool holder 312. A actuation portion 348 of the clamping member 328 is configured to be pressed to overcome the biasing force applied by the biasing element 352 to pivot the clamping head element 336 away from the mounting structure 316 in order to selectively secure or remove an accessory tool between the tool holder 312 and the clamping head element 336.

Figure 10:
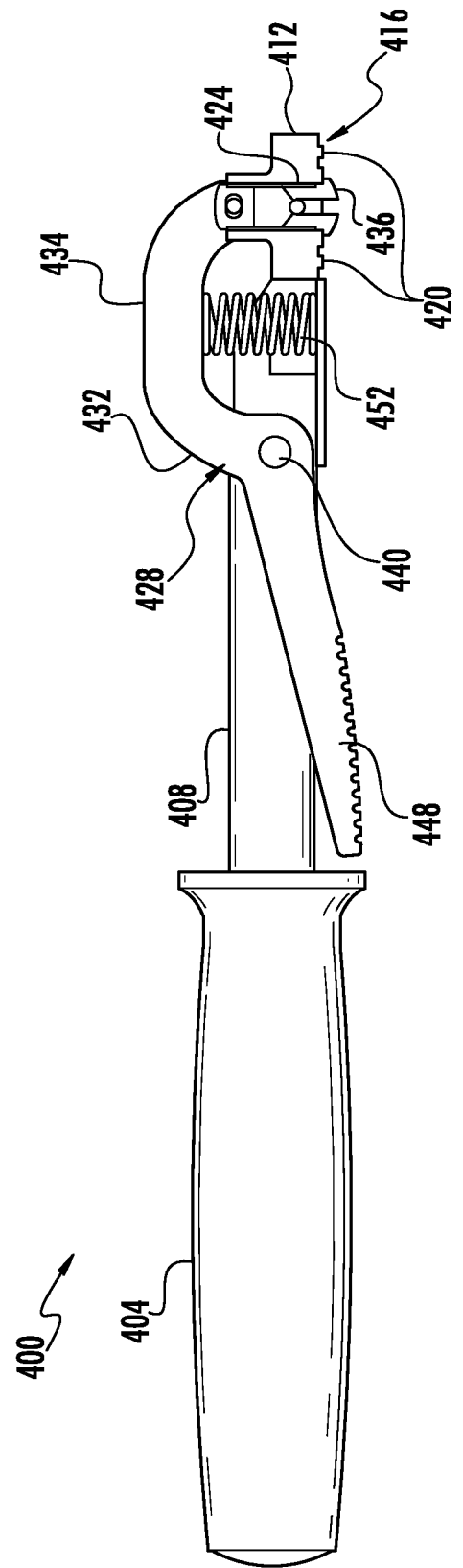
FIG. 10 depicts a side perspective view of an embodiment of a handheld tool assembly having a clamping mechanism shown in a locked positioned that is pivotable about a horizontal axis with a lever arm in order to selectively secure an accessory tool.

FIG. 10 depicts another embodiment of a handheld tool assembly configured to enable manual operation of an accessory tool. The handheld tool assembly 400 includes a handle 404 fixedly secured to a tool shaft 408. The end of the tool shaft 408 includes a tool holder 412 having a mounting structure 416. The mounting structure 416 includes a plurality of protrusions 420 arranged in a circular pattern about a central bore 424 that are sized, shaped, and positioned complementary to the openings or recesses 46 (FIG. 25) and the central opening 48 of the accessory mounting structure 44 of the accessory tool 12.

The handheld tool assembly 400 further includes a clamping member 428 configured to secure an accessory tool (not shown) to the mounting structure 416. The clamping member 428 comprises a shaft section 432 having an actuating lever 448 and clamping section 434 with a clamping head element 436. The shaft section 432 is pivotably mounted to the tool shaft 408 with a pin 440 that extends through the shaft section 432 and the tool shaft 408. The shaft section 432 is pivotably biased in a counterclockwise direction with respect to the orientation shown in FIG. 10 with a biasing element 452 to a locked position as shown. Without an accessory tool placed on the retaining structure 416 as shown in FIG. 10, the clamping head element 436 is pulled tightly against the tool holder 412 in the locked position.

In order to secure an accessory tool 12 to the tool holder 412, the actuation lever 448 is pulled upwards with respect to the orientation of the handheld tool assembly 400 shown in FIG. 10, which pivots the clamping portion 434 clockwise. The movement unseats the clamping head element 436 from the tool holder 412. An accessory tool (not shown), such as the accessory tool 12 of FIG. 25 may then be positioned on the mounting structure 416 with the clamping head element 436 extending through the central opening 48 (FIG. 25) of the accessory tool 12, and the protrusions 420 cooperating within the openings or recesses 46 (FIG. 25) of the accessory tool 12. The actuation lever 448 is then released, allowing the biasing element 452 to pivot the shaft section 432 in a counterclockwise direction until the clamping head 436 contacts the accessory tool (not shown). The biasing element 452 ensures that the clamping head element 436 applies a sufficient force against the accessory tool (not shown) to ensure that the accessory tool is secured to the tool holder 412. The actuation lever 448 can then be pulled upwards to pivot the clamping head 436 to a position out of contact with the accessory tool in which the accessory tool can be removed from the cool holder 412.

FIGS. 11-13 depict another embodiment of a handheld tool assembly configured to enable manual operation of an accessory tool. Referring to FIG. 11, a handheld tool assembly 500 includes a handle 504 fixedly secured to a tool shaft 508. A tool holder 512 is fixedly connected to the end of the tool shaft 508. As best shown in FIG. 12, the tool holder 512 includes a having a plurality of protrusions 520 arranged in a circular pattern about a tab 524 that are sized, shaped, and positioned complementary to the openings or recesses 46 (FIG. 25) and the central opening 48 of the accessory mounting structure 44 of the accessory tool 12.

Returning to FIG. 11, the handheld tool assembly 500 further includes a clamping member 528 configured to secure an accessory tool (not shown) to the tool holder 512. Referring to FIG. 13 which shows the clamping member 528 removed from the handheld tool assembly 500 for clarity, the clamping member 528 comprises a lever arm 548, a clamping head element 536, a locking hook 538 defining a lock slot 539, and a pin opening 540. Returning again to FIG. 11, the clamping member 528 is pivotably mounted to the tool shaft 508 with a pivot pin 541 positioned through the tool shaft 508 and the pin opening 540 (FIG. 13) of the clamping member 528. A locking pin 554 is positioned in a slot 556 in the tool shaft 508, and configured to be moved translationally within the slot 556 to a locked position and an unlocked position. The locking pin 554 is biased by a biasing element 552 to the left with respect to the orientation shown in FIG. 11.

The clamping member 528 is configured to be biased between a locked position as shown in FIG. 11 in which an accessory tool (not shown) is secured by the clamping had element 536 to the tool holder 512, and an unlocked position (not shown) where the accessory tool may be freely removed from or placed on the tool holder 512. In the locked position shown in FIG. 11, the clamping head element 536 pressed tightly against the mounting portion of an accessory tool (not shown) positioned on the mounting structure 516. The biasing element 552 forces the locking pin 554 leftward in the slot 556 of the tool shaft 508 within the lock slot 539 of the locking hook 538. The clamping member 528 is thereby prevented from pivoting about the pin 540 to an unlocked position due to the engagement of the locking pin 554 with the locking hook 538.

In order to pivot the clamping member 528 to an unlocked position so that an accessory tool (not shown) may be removed from or placed on the tool holder 512, the locking pin 554 is manually translated to the right with respect to the orientation of the handheld tool assembly 500 shown in FIG. 11 to overcome the force applied by the biasing element 552 until the locking pin is positioned outside of the lock slot 539 of the locking hook 538. In this position, the lever arm 548 can be freely pressed downwards without the locking pin 554 contacting the locking hook 538 in order to pivot the clamping head element 536 to an unlocked position (not shown) out of engagement with the accessory tool (not shown) or the tool holder 512.

Figure 14:
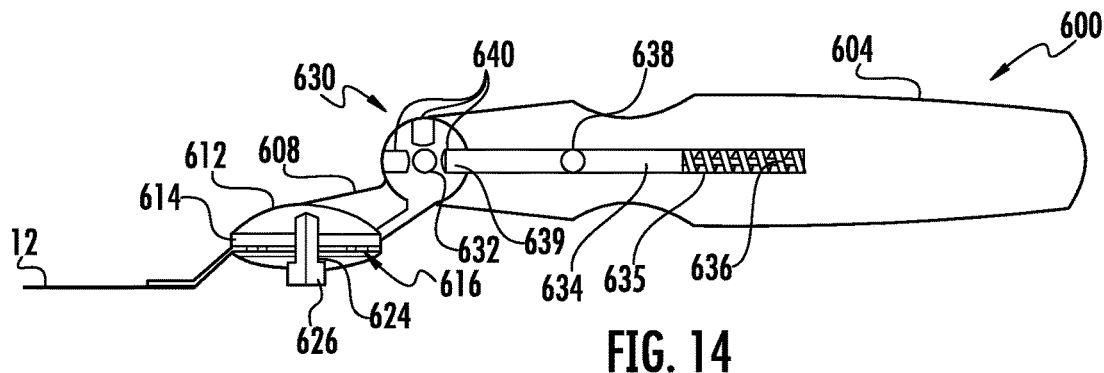
FIG. 14 depicts a side cross-sectional view of another embodiment of a handheld tool assembly with an accessory tool secured to a tool holder that is rotatable about a horizontal axis with respect to the handle and locked at selectable angular positions, shown with the accessory tool and tool holder locked in a first angular position.
Figure 15:
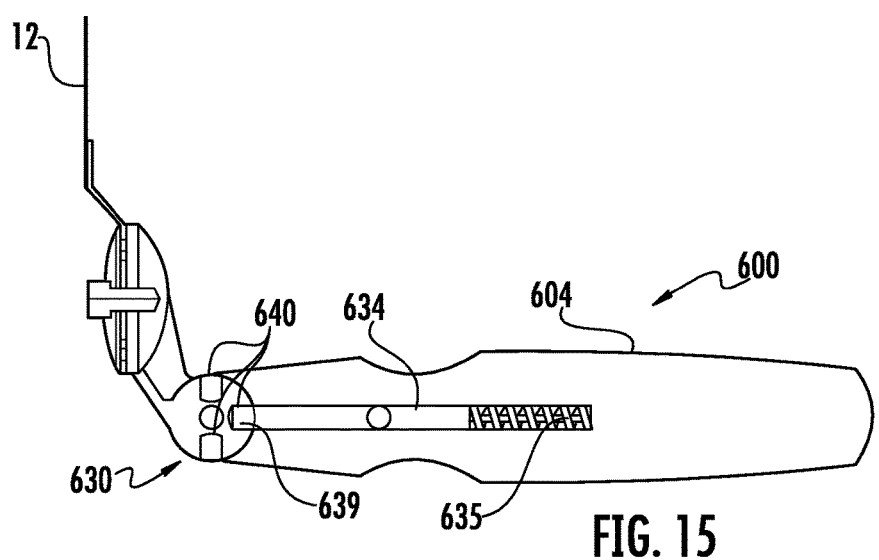
FIG. 15 depicts a side cross sectional view of the handheld tool assembly of FIG. 14 with the accessory tool and tool holder locked in a second angular position.

FIG. 14-15 shows another embodiment of a handheld tool assembly configured to enable manual operation of an accessory tool and further enable the accessory tool to be. A handheld tool assembly 600 includes a handle 604 and a tool shaft 608 rotatably secured to the handle 604 with a pivot mechanism 630. The tool shaft 608 includes a tool holder 612 having a mounting structure 616. The tool holder 612 includes a slot 614 configured to receive the mounting structure 44 of the accessory tool 12 (FIG. 25), and a plurality of protrusions 620 arranged in a circular pattern (not shown) about a central bore 624 that are sized, shaped, and positioned complementary to the openings or recesses 46 (FIG. 25) and the central opening 48 of the accessory mounting structure 44 of the accessory tool 112. The tool holder 612 further includes a clamping element 626 configured to retain the accessory tool within the slot 614. In the embodiment shown, the clamping element 626 includes external threads (not shown) configured to mate with corresponding internal threads (not shown) of the central bore 624. The clamping element 626 is rotated to tighten the accessory tool securely in the slot 614.

The pivot mechanism 630 enables the tool shaft 608 to be selectably pivoted with respect to the handle 604 about a horizontal axis and selectably locked at incremental angular positions, such as a first angular position shown in FIG. 14, and a second angular position shown in FIG. 15. The pivot mechanism includes a pin 632 extending through openings (not shown) in the handle 604 and the pivot mechanism 630. A lock rod 634 configured to hold the tool shaft 608 at each angular orientation is positioned within a slot 635 defined within the handle 604. A biasing element 636 also positioned within the slot 635 biases the lock rod 634 outwardly to urge an end 639 of the lock rod 639 into one of the lock openings 640 located radially about the pivot mechanism 630. The lock openings 640 are configured to receive the end 639 of the lock rod 634 in order to lock the tool shaft 608 with respect to the handle 604 at a desired angular position. In the embodiment shown, four openings 640 are defined in the pivot mechanism 630 approximately 90 degrees apart from each other to allow selective angular positioning of the tool shaft 608 with respect to the handle 604 at increments approximately 90 degrees apart. However, any desired number of openings 640 may be defined in the pivot mechanism 630 with any desired angular spacing in order to establish the incremental angular positions in which the tool shaft 608 may be locked at.

In order to change the angular position of the tool shaft 608, a rod handle 638 extending radially from the lock rod 634 is pulled to the right with respect to the orientation shown in FIG. 14 to move the lock rod 634 inwardly against the biasing force of the biasing element 636 until the end 639 of the lock rod 634 is fully removed from an opening 640. The tool shaft 608 with the pivot mechanism 630 is then rotated about the in pin 632 to a desired angular position in which another one of the openings 640 is aligned with the lock rod 634. The rod handle 638 is then released, and the biasing element 636 urges the end 639 of the lock rod 634 into an opening 640 corresponding to the selected angular position of the tool shaft 608.

Figure 16:
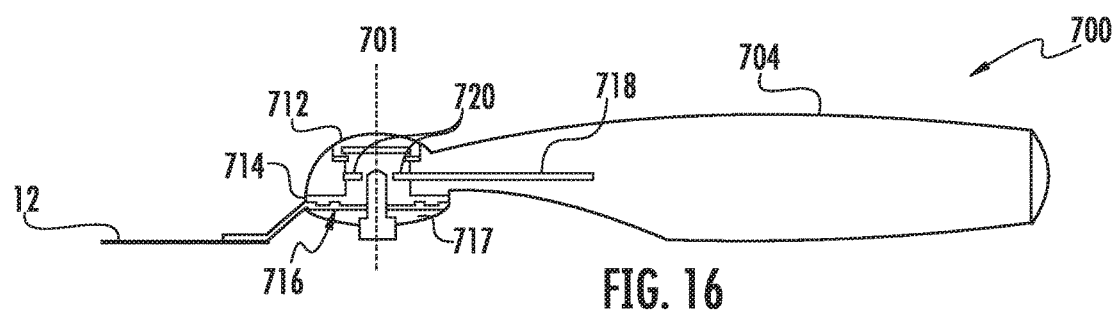
FIG. 16 depicts a side cross-sectional view of another embodiment of a handheld tool assembly with an accessory tool secured to a tool holder that is rotatable about a vertical axis with respect to the handle to various selectable angular positions.

While the embodiment of the handheld tool assembly 600 shown in FIGS. 14-15 provides for rotation of the tool shaft 608 about a radial axis of the handle 604, the handheld tool assembly 700 of FIG. 16 provides a similar mechanism for providing selective angular positioning of the accessory tool 12 about a vertical axis 701 extending through the center of the accessory tool 12. The handheld tool assembly 700 includes a handle 704 and a tool holder 712 defining a slot 714 and having a rotating lower structure 717 with a mounting structure 716 configured to retain the accessory tool 12. A stop rod 718 is configured to extend through one of a plurality of openings 720 (two shown in FIG. 16) similarly to the stop rod 634 within the openings 620 of FIGS. 14-15, to maintain an angular position of the rotating lower structure 717 and the accessory tool 12 with respect to the handle 704. Similar to the stop rod 634 and the openings 640 of the handheld tool assembly 600, the stop rod 718 is removed, the lower structure 717 with the accessory tool 12 is rotated, and the stop rod 718 is placed back through an opening 720 in order to change the angular position of the accessory tool 12 with respect to the handle.

Figure 17:
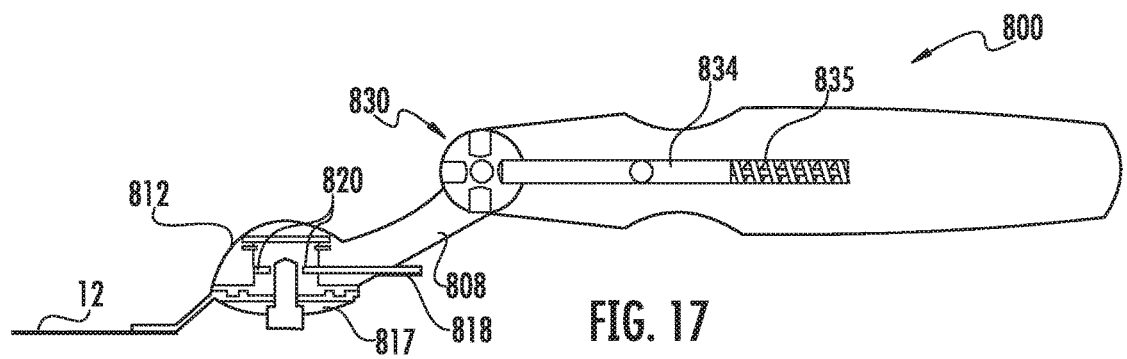
FIG. 17 depicts a side cross-sectional view of another embodiment of a handheld tool assembly with an accessory tool and tool holder that is rotatable about both a horizontal axis and a vertical axis with respect to the handle to various selectable angular positions.

Turning to the embodiment of the handheld tool assembly of FIG. 17, the handheld tool assembly 800 includes a pivot mechanism 830 with a stop rod 834 and biasing element 835 substantially similar to the pivot mechanism 630, stop rod 634 and biasing element 635, respectively, of the handheld tool assembly 600, and a tool holder 812 with a rotatable lower structure 817 with openings 820 and a stop rod 818 substantially similar to the tool holder 712, the rotatable lower structure 717, openings 720 and stop rod 718 of the handheld tool assembly 700. The handheld tool assembly 800 thus provides for two degrees of selective angular positioning substantially by incorporating the rotational movements of both of the handheld tool assemblies 600 and 700, the operation of which has already been described in connection with those embodiments.

Figure 18:
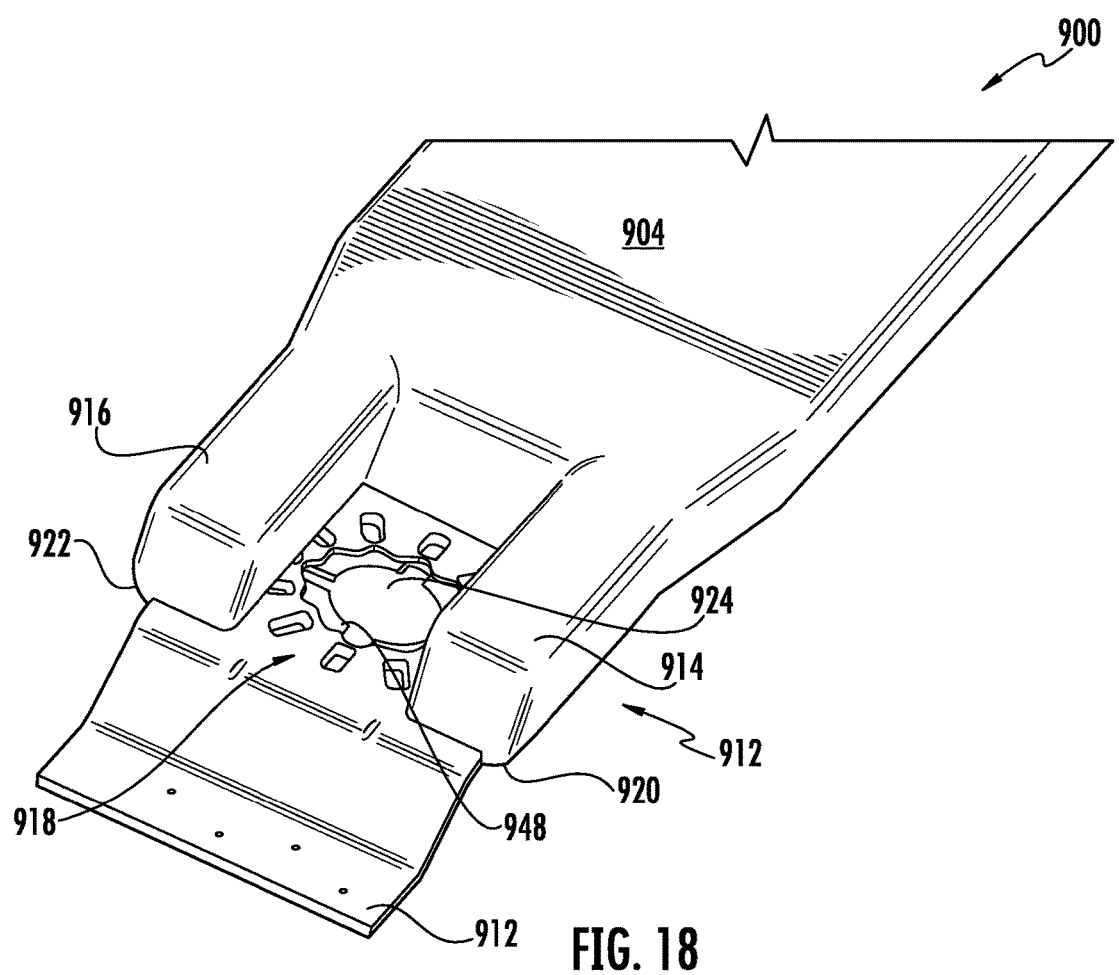
FIG. 18 depicts a perspective view of another embodiment of a handheld tool assembly with an accessory tool mounted to a mounting structure between a pair of mounting arms.

FIG. 18 depicts another embodiment of a handheld tool assembly configured to enable manual operation of an accessory tool. A handheld tool assembly 900 includes a handle 904 with a tool holder 912. The tool holder 912 includes two arms 914, 916 defining an opening 918 therebetween. A slot 920 is defined in the arm 914, and a slot 922 is defined in the arm 916. The slots 920, 922 are configured to receive an accessory tool, such as the accessory tool 912 shown. The tool holder 912 further includes a lower structure (not visible) with a tab 924 configured to mate with the opening 948 of the accessory tool 912 shown.

In order to secure an accessory tool, such as the accessory tool 912 shown, to the tool holder 912, a leading edge of a mounting end of the accessory tool is placed through the slots 920, 922 and into the opening 918 between the arms 914, 916 and the lower structure (not visible). In one embodiment, the arms 914, 916 are designed to slightly flex to allow the leading edge of the accessory tool to be pushed over the tab 924, until the tab 924 aligns with the opening 948 of the accessory tool. The arms 914, 916, tab 924 and lower structure (not visible) hold the accessory tool to the handle 904.

Figure 19:
FIG. 19 depicts a side perspective view of the clamping mechanism of the handheld tool assembly of FIGS. 8-9.
Figure 20:
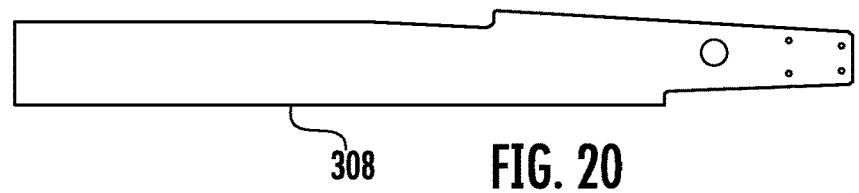
FIG. 20 depicts a side perspective view of the tool shaft of the handheld tool assembly of FIGS. 8-9.
Figure 21:
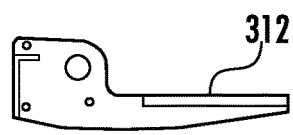
FIG. 21 depicts a side perspective view of the tool holder of the handheld tool assembly of FIGS. 8-9.
Figure 22:
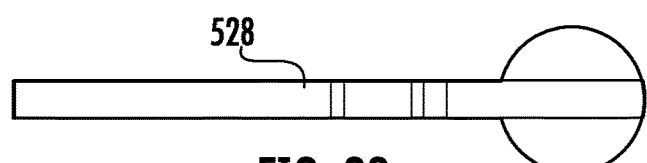
FIG. 22 depicts a top perspective view of the clamping mechanism of the handheld tool assembly of FIGS. 11-13.
Figure 23:
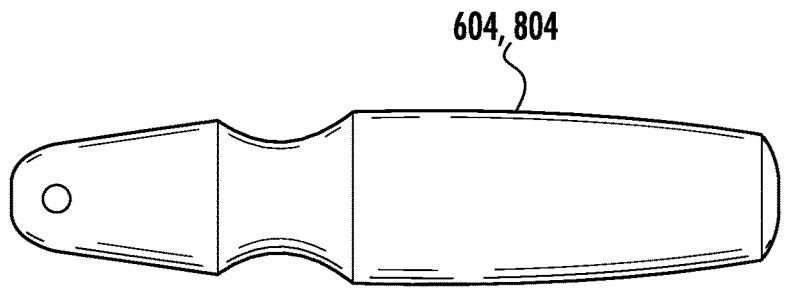
FIG. 23 depicts a side perspective view of the handle of the embodiments of the handheld tool assembly of FIGS. 14, 15 and 17.

Various elements of embodiments of the handheld tool assemblies are shown in FIGS. 19-23 for clarity. Specifically, FIG. 19 shows the clamping member 328 of the handheld tool assembly 300 of FIGS. 8-9 disconnected from the tool shaft 308 (FIGS. 8-9), FIG. 20 shows the tool shaft 308 disconnected from the handle 304 (FIGS. 8-9), and FIG. 21 shows the tool holder 312 disconnected from the tool shaft 308 (FIGS. 8-9). FIG. 22 shows the clamping member 528 of the handheld tool assembly 500 of FIGS. 11-12 disconnected from the tool shaft 508 (FIGS. 11-12). FIG. 23 shows the handle 604, 804 of the handheld tool assemblies 600 and 800 of FIGS. 14-15 and 17 disconnected from the pivot mechanism.

While embodiments have been illustrated and described in detail in the drawings and foregoing description, the same should be considered as illustrative and not restrictive in character. It is understood that exemplary embodiments have been presented and that all changes, modifications and further applications that come within the spirit of the disclosure are desired to be protected.

What is claimed is:

1. A tool system, comprising:
an accessory tool including a working end and a mounting end extending from the working end, the mounting end defining a plurality of openings arranged in a desired configuration;
an oscillating power tool including a first tool holder having a first mounting structure including a first plurality of protrusions arranged in the desired configuration and configured to be received by the plurality of openings to connect the mounting end of the accessory tool to the oscillating power tool; and
a handheld tool assembly including a second tool holder having a second mounting structure including a second plurality of protrusions arranged in the desired configuration and configured to be received by the plurality of openings to connect the mounting end of the accessory tool to the handheld tool assembly.

2. The system of claim 1, wherein the handheld tool assembly comprises:
a tool shaft; and
a handle extending from a first end of the tool shaft,
wherein at least a portion of the second tool holder extends from a second end of the tool shaft opposite of the first end,
wherein movement of the accessory tool relative to the handle is prevented when the second tool holder is connected to the mounting end.

3. The system of claim 2, wherein the second tool holder comprises:
a threaded bore located in a center of the second plurality of protrusions; and
a clamping member including a threaded pin configured to be threadingly connected to the threaded bore, wherein the second tool holder is connected to the mounting end of the accessory tool when the second plurality of protrusions are received by the plurality of openings and the threaded pin is threadingly connected to the threaded bore.

4. The system of claim 3, wherein the clamping member further comprises:
a knob extending from an opposite side of the clamping member from the threaded pin.

5. The system of claim 2, wherein the second tool holder comprises:
a clamping member pivotably connected to the tool shaft and configured for movement to a clamped position and an unclamped position, the clamping member including a clamping head configured (i) to clamp the mounting end against the second mounting structure in response to the clamping member being in the clamped position, and (ii) to unclamp the mounting end to enable removal of the accessory tool from the second mounting structure in response to the clamping member being in the unclamped position.

6. The system of claim 5, wherein the second tool holder further comprises:
an actuation mechanism including a button movable to a locked position and an unlocked position, and a biasing member configured to bias the button toward the locked position,
wherein the actuation mechanism prevents movement of the clamping member from the clamped position to the unclamped position when button is in the locked position, and
wherein the actuation mechanism enables movement of the clamping member from the clamped position to the unclamped position when the button is in the unlocked position.

7. The system of claim 5, further comprising:
a biasing member configured to bias the clamping member in the clamped position.

8. The system of claim 7, wherein:
the clamping member is configured to pivot about a pin, and
the pin is located between the biasing member and the second mounting structure.

9. The system of claim 7, wherein:
the clamping member is configured to pivot about a pin, and
the biasing member is located between the pin and the second mounting structure.

10. The system of claim 5, further comprising:
a locking pin located in a slot defined by the tool shaft and slidable to a locked position and an unlocked position; and
a locking hook extending from the clamping member, the locking hook configured to engage the locking pin in response to the clamping member being in the clamped position and the locking pin in the locked position to prevent movement of the clamping member from the clamped position to the unclamped position.

11. The system of claim 2, further comprising:
a pivot mechanism located between the handle and the second tool holder and configured to enable movement of the second tool holder relative to the handle.

* * * * *